(12) United States Patent
Giannetti et al.

(10) Patent No.: US 6,866,668 B2
(45) Date of Patent: Mar. 15, 2005

(54) METHODS, INSTRUMENTS AND MATERIALS FOR CHONDROCYTE CELL TRANSPLANTATION

(75) Inventors: Bruno Giannetti, Bonn (DE); Peter Behrens, Lübeck (DE); Samuel Asculai, Toronto (CA)

(73) Assignee: Verigen Transplantation Service International ("VTSL") AG, Leverkusen (DE)

( * ) Notice: Subject to any disclaimer, the term of this patent is extended or adjusted under 35 U.S.C. 154(b) by 0 days.

(21) Appl. No.: 09/859,370

(22) Filed: May 17, 2001

(65) Prior Publication Data

US 2002/0045940 A1 Apr. 18, 2002

Related U.S. Application Data

(63) Continuation of application No. 09/373,952, filed on Aug. 13, 1999, now abandoned.
(60) Provisional application No. 60/146,683, filed on Aug. 2, 1999, and provisional application No. 60/096,597, filed on Aug. 14, 1998.

(51) Int. Cl.[7] .............................................. A61B 17/58
(52) U.S. Cl. ...................................................... 606/99
(58) Field of Search .......................... 606/99, 127, 108, 606/110, 113, 114, 206, 209, 211

(56) References Cited

U.S. PATENT DOCUMENTS

| | | | | |
|---|---|---|---|---|
| 2,670,519 A | * | 3/1954 | Recklitis | ..................... 27/24.2 |
| 3,989,049 A | * | 11/1976 | Yoon | ........................... 128/831 |
| 4,174,715 A | * | 11/1979 | Hasson | ........................ 606/206 |
| 4,374,523 A | * | 2/1983 | Yoon | ........................... 606/141 |
| 4,385,404 A | | 5/1983 | Sully et al. | |
| 4,393,872 A | * | 7/1983 | Reznik et al. | ............... 604/264 |
| 4,393,874 A | | 7/1983 | Nappholz et al. | |
| 4,553,272 A | | 11/1985 | Mears | |
| 4,559,936 A | | 12/1985 | Hill | |
| 4,611,594 A | * | 9/1986 | Grayhack et al. | ........... 606/127 |

(List continued on next page.)

FOREIGN PATENT DOCUMENTS

| | | |
|---|---|---|
| DE | 29 33 174 | 4/1980 |
| DE | 44 25 456 | 3/1996 |

(List continued on next page.)

OTHER PUBLICATIONS

Archer, Charles, W.; McDowell, Jenny; Bayliss, Michael, T.; Stephens, Myra, D.; and Bentley, George, "Phenotypic modulation in sub–populations of human articular chondrocytes in vitro," Journal of Cell Science, vol. 97, 1990, pp. 361–371.

(List continued on next page.)

*Primary Examiner*—Eduardo C. Robert
(74) *Attorney, Agent, or Firm*—Morgan, Lewis & Bockius LLP

(57) ABSTRACT

A method for the effective treatment of articulating joint surface cartilage in an animal by the transplantation of an implantable article including chondrocyte cells retained to an absorbable support matrix. An instrument for placing and manipulating the implantable article at the site of implantation, and a retention device for securing the implantable article to the site of implantation. An implantable article for cartilage repair in an animal, the implantable article including chondrocyte cells retained on an absorbable support matrix, and a method of making same. An article comprising an absorbable flexible support matrix for living cells grown and adhered thereto.

1 Claim, 14 Drawing Sheets

U.S. PATENT DOCUMENTS

| | | | |
|---|---|---|---|
| 4,642,117 A | | 2/1987 | Nguyen et al. |
| 4,642,120 A | | 2/1987 | Nevo et al. |
| 4,649,918 A | | 3/1987 | Pegg et al. |
| 4,657,020 A | * | 4/1987 | Lifton .................. 606/106 |
| 4,681,588 A | | 7/1987 | Ketharanathan |
| 4,789,663 A | | 12/1988 | Wallace et al. |
| 4,846,835 A | | 7/1989 | Grande |
| 4,877,020 A | | 10/1989 | Vich |
| 4,904,259 A | | 2/1990 | Itay |
| 5,019,108 A | | 5/1991 | Bertin et al. |
| 5,041,138 A | | 8/1991 | Vacanti et al. |
| 5,062,845 A | | 11/1991 | Kuslich et al. |
| 5,067,964 A | | 11/1991 | Richmond et al. |
| 5,092,883 A | | 3/1992 | Eppley et al. |
| 5,116,374 A | | 5/1992 | Stone |
| 5,147,378 A | * | 9/1992 | Markham .................. 606/206 |
| 5,158,574 A | | 10/1992 | Stone |
| 5,190,561 A | * | 3/1993 | Graber .................. 606/127 |
| 5,201,745 A | | 4/1993 | Tayot et al. |
| 5,206,023 A | | 4/1993 | Hunziker |
| 5,206,028 A | | 4/1993 | Li |
| 5,246,441 A | | 9/1993 | Ross et al. |
| 5,258,043 A | | 11/1993 | Stone |
| 5,259,835 A | | 11/1993 | Clark et al. |
| 5,306,311 A | | 4/1994 | Stone et al. |
| 5,337,754 A | * | 8/1994 | Heaven et al. .............. 600/562 |
| 5,354,283 A | | 10/1994 | Bark et al. |
| 5,403,338 A | | 4/1995 | Milo |
| 5,423,858 A | | 6/1995 | Bolanos et al. |
| 5,445,597 A | | 8/1995 | Clark et al. |
| 5,470,911 A | | 11/1995 | Rhee et al. |
| 5,544,552 A | | 8/1996 | Kirsch et al. |
| 5,567,806 A | | 10/1996 | Abdul-Malak et al. |
| 5,569,252 A | | 10/1996 | Justin et al. |
| 5,658,343 A | | 8/1997 | Hauselmann et al. |
| 5,667,525 A | * | 9/1997 | Ishibashi .................. 606/206 |
| 5,713,374 A | | 2/1998 | Pachence et al. |
| 5,736,372 A | | 4/1998 | Vacanti et al. |
| 5,759,190 A | | 6/1998 | Vibe-Hansen et al. |
| 5,769,899 A | | 6/1998 | Schwartz et al. |
| 5,837,278 A | | 11/1998 | Geistlich et al. |
| 5,853,746 A | | 12/1998 | Hunziker |
| 5,902,741 A | | 5/1999 | Purchio et al. |
| 5,932,459 A | | 8/1999 | Sittinger et al. |
| 5,989,269 A | | 11/1999 | Vibe-Hansen et al. |
| 6,007,539 A | | 12/1999 | Kirsch et al. |
| 6,080,194 A | | 6/2000 | Pachence et al. |
| 6,132,463 A | | 10/2000 | Lee et al. |
| 6,143,501 A | | 11/2000 | Sittinger et al. |
| 6,187,053 B1 | | 2/2001 | Minuth |
| 6,270,505 B1 | * | 8/2001 | Yoshida et al. ............. 606/127 |
| 6,383,195 B1 | * | 5/2002 | Richard .................. 606/114 |

FOREIGN PATENT DOCUMENTS

| | | |
|---|---|---|
| DE | 196 54 884 A1 | 10/1997 |
| DE | 196 48 876 | 5/1998 |
| EP | 0 308 238 | 3/1989 |
| EP | 0 339 607 B1 | 11/1989 |
| EP | 0 361 896 | 4/1990 |
| EP | 0 375 127 | 6/1990 |
| EP | 0530 804 | 3/1993 |
| EP | 0 640 647 A2 | 3/1995 |
| EP | 0 674 908 A1 | 10/1995 |
| EP | 0 842 670 A1 | 5/1998 |
| FR | 2 679 778 A1 | 2/1993 |
| GB | 2 226 247 B | 9/1988 |
| WO | WO 86/00526 | 1/1986 |
| WO | WO 88/06894 | 9/1988 |
| WO | WO 89/01767 | 3/1989 |
| WO | WO 89/04646 | 6/1989 |
| WO | WO 90/05755 | 5/1990 |
| WO | WO 90/09783 | 9/1990 |
| WO | WO 90/10018 | 9/1990 |
| WO | WO 90/13302 | 11/1990 |
| WO | WO 92/13565 | 8/1992 |
| WO | WO 92/22312 | 12/1992 |
| WO | WO 93/11723 | 6/1993 |
| WO | WO 93/19168 | 9/1993 |
| WO | WO 94/00484 | 1/1994 |
| WO | WO 94/09118 | 4/1994 |
| WO | WO 94/09722 | 5/1994 |
| WO | WO 95/18638 | 7/1995 |
| WO | WO 95/30383 | 11/1995 |
| WO | WO 96/03093 | 2/1996 |
| WO | WO 96/24310 | 8/1996 |
| WO | WO 96/25961 | 8/1996 |
| WO | WO 96/39196 | 12/1996 |
| WO | WO 97/26028 | 7/1997 |
| WO | WO 97/30662 | 8/1997 |
| WO | WO 97/32616 | 9/1997 |
| WO | WO 97/46665 | 12/1997 |
| WO | WO 98/08469 | 3/1998 |
| WO | WO 98/35653 | 8/1998 |
| WO | WO 99/19005 | 4/1999 |

OTHER PUBLICATIONS

Aulthouse, Amy Lynn; Beck, Michael; Griffey, Edward; Sanford, Julie; Arden, Karen; Machado, Mirta, A.; and Horton, William, A., "Expression of the Human Chondrocyte Phenotype in Vitro", In Vitro Cellular and Developmental Biology, vol. 25, No. 7, Jul. 1989, p. 659–668.

Benya, Paul D.; Padilla, Silvia, R.; and Nimni, Marcel, E., "Independent Regulation of Collagen Types by Chondrocytes during the Loss of Differentiated Function in Culture", Cell, vol. 15, Dec. 1978, pp. 1313–1321.

Bonaventure, J.; Kadhorn, N.; Cohen–Solal, L.; Ng, K.H.; Bourguignon, J.; Lasselin, C.; and Freisinger, P., "Reexpression of Cartilage–Specific Genes by Dediffrentiated Human Articular Chondrocytes Cultured in Alginate Beads," Experimental Cell Research, vol. 212, 1994, pp. 97–104.

Brittberg, M., M.D.; Nilsson, Anders, M.D., Ph.D.; Lindalhl, A., M.D., Ph.D., Ohlsson, C., M.D., Ph.D.; and Peterson, L., M.D., Ph.D., "Rabbit Articular Cartilage Defects Treated With Autologous Cultured Chondrocytes," Clinical Orthopaedics and Related Research, No. 326, 1996, pp. 270–283.

Brittberg, M., M.D.; Lindahl, A., M.D., Ph.D.; Nilsson, A., M.D., Ph.D.; Ohlsson, C.; M.D., Ph.D; Isaksson, O., M.D., Ph.D.; and Peterson, L., M.D., Ph.D., "Treatment of Deep Cartilage Defects in the Knee with Autologous Chondrocyte Transplantation," New England Journal of Medicine, vol. 331, No. 14, Oct. 6, 1994, pp. 889–895.

Bujia, J.; Sittinger, M.; Hammer, C.; and Burmester, G., "Engineering Human Cartilage Tissue Using a Perfusion Chamber," Laryngo–Rhino–Otol., vol. 73, 1994, pp. 577–580. (Abstract in English).

Bujia, J., "In Vitro Engineering of Autologous Cartilage Tissue for Reconstructive Surgery: Possiblities and Limitations," Laryngo–Rhino–Otol., vol. 75, 1995, pp. 205–210. (Abstract in English).

Cahn, Robert D. and Lasher, Robert, "Simultaneous Synthesis of DNA and Specialized Cellular Products by Differenting Cartilage Cells in Vitro," PNAS, vol. 58, 1967, pp. 1131–1138.

Coon, H.G. and Cahn, R.D., "Differentiation in vitro: Effects of Sephadex Fractions of Chick Embryo Extract," Science, vol. 153, Sep. 2, 1966, pp. 116–1119.

Ficat, R.P., M.D.; Ficat, C., M.D.; Gedeon, P., M.D.; and Toussaint, J.B., M.D., "Spongialization: A New Treatment for Diseased Patellae," Clinical Orthopaedics and Related Research, No. 1444, Oct. 1979, pp. 74–83.

Freed, L. et al., Joint Resurfacing Using Allograft Chondrocytes and Synthetic Biodegradable Scaffolds, J. Biomed. Mater. Res. 1994, 28(8):891–899.

Frenkel, Sally, R.; Toolan, Brian; Menchie, David; Itman, Mark, I; and Pachence, James, R., "Chondrocyte Transplantation Using a Collagen Bilayer Matrix for Cartilage Repair," The Journal of Bone and Joint Surgery, vol. 79–B, No. 5, Sep. 1997, pp. 831–836.

Fujisato et al., "Effect of Basic Fibroblast Growth Factor on Cartilage Regeneration in Chondrocyte–seeded collagen Sponge Scaffold," Biomaterials, 1996, 17:155–162.

Gospodarowicz et al., "A comparison of the Responses of Cultured Myoblasts and Epidermal Growth Factors", J. Cell. Physiol., 1977, 93: 117–128.

Hall et al., "Cartilage: Molecular Aspects", Biomed, 1991, pp. 42–57.

Hauselmann, Hans, J.; Fernandes, Russel, J.; Mok, Su, S.; Schmid, Thomas, M.; Block, Joel, A.; Aydelotte, Margaret, B.; Kuettner, Klause, E.; and Thonar, J.–M., A., "Phenotypic stability of bovine articular chondrocytes after long–term culture in alginate beads," Journal of Cell Science, vol. 107, 1994, pp. 17–27.

Helbing, G.; Burri, C.; Heit, W.; Neugebauer, R.; and Ruter, A., "In vivo synthesis of cartilage after transplantation of chondrocytes in animal experiments," Chir Forum Exp Klin Forsch, 1980, pp. 47–51. (Abstract in English).

Hendrickson, D.A.; Nixon, A.J.; Grande, D.A.; Todhunter, R.J.; Minor, R.M.; Erb, H.; and Lust, G., "Chondrocyte–Fibrin Matrix Transplants for Resurfacing Extensive Articular Cartilage Defects," Journal of Orthopaedic Research, vol. 12, No. 4, 1994, p. 485–497.

Hinek, A.; Kawiak, J.; Czarnowska, E.; and Barcew, B., "The Effect of Agarose and Dexamethasone on the Nature and Production of Extracellular Matrix Components by Elastic Cartilage Chondrocytes," Acta Biologica Hungarica, vol. 35, 1984, pp. 245–258.

Insall, J., M.D., "The Pridie Debridement Operation for Osteoarthritis of the Knee," Clinical Orthopaedics and Related Research, No. 101, Jun. 1974, pp. 61–67.

International Search Report dated Dec. 23, 1999.

International Search Report dated Mar. 3, 2000.

Ishizeki, K.; Nagano, H.; Fujiwara, H.; and Nawa, T., "Morphological changes during survival, cellular transformation, and calcification of the embryonic mouse: Meckel's cartilage transplanted into heterotopic sites," J. Carniofac Genet Dev. Biol, vol. 14, 1994, pp. 33–42.

Johnson, L.L., "Arthroscopic Abrasion Arthroplasty," Operative Arthroscopy, edited by J.B. McGinty et al., Raven Press, New York, 1991, Chapter 24, pp. 341–360.

Kandel, R.A., M.D.; Chen, H., M.Sc.; Clark, J.; and Renlund, R., D.V.M., M.Sc., "Transplantation of Cartilagenous Tissue Generated In Vitro Into Articular Joint Defects," Art. Cells, Blood Subs., and Immob. Biotech., vol. 23(5), 1995, pp. 565–577.

Kawabe, N., M.D.; Ehrlich, M.G., M.D.; and Mankin, H.J., M.D., "Growth Plate Reconstruction Using Chondrocyte Allograft Transplants," Journal of Pediatric Orthopaedics, vol. 7, 1987, pp. 381–388.

Kawiak, J.; Moskalewski, S.; and Hinek, J., "Reconstruction of the elastic cartilage by isolated chondrocytes in autogeneic transplants," Acta anat., vol. 76, 1970, pp. 530–544.

Kempson, G. E.; Tuke, M. A.; Dingle, J. T.; Barrett, A. J.; and Horsfield, P.H. "The Effects of Proteolytic Enzymes on the Mechanical Properties of Adult Human Articular Cartilage", Biochimica et Biophysica Acta, vol. 428, 1976, pp. 741–760.

Kirsch, T.; Swoboda, Bernd; and Von Der Mark, K., "Ascorbate independent differentiation of human chondrocytes in vitro: simultaneous expression of types I and X collagen and mitrix minerlization," Differentiation, vol. 52, 1992, pp. 89–100.

Kolettas, E.; Buluwela, L.; Bayliss, M.T.; and Muir, H.I.; "Expression of cartilage–specific molecules is retained on long–term culture of human articular chondrocytes," Journal of Cell Science, vol. 108, 1995, pp. 1991–1999.

Ksander et al., "Exogenous Transforming Growth Factor–Beta 2 Enhances Connective Tissue Formation and Wound Strength in Guinea Pig Dermal Wounds Healing By Secondary Intent," Annals of Surgery, vol. 211, No. 3, Mar. 1990, pp. 288–294, *Abstract; discussion.

Ksiazek, Tomasz, Ph.D. and Moskalewski, S.; Ph.D.; "Studies on Bone Formation by Cartilage Reconstructed by Isolated Epiphyseal Chondrocytes, Transplanted Syngeneically or Across Known Histocompatibility Barriers in Mice," Clinical Orthopaedics and Related Research, No. 172, Jan.–Feb. 1983, pp. 233–242.

Miller, M.D., "Treatment of Chondral Injuries", Operative Techniques in Orthopaedics, vol. 7, No. 4, Oct., 1997.

Minas, et al., "Chondrocyte Transplantation", Operative Techniques in Orthopaedics, vol. 7, p. 323–333 (1997).

Moskalewski, S.; Hyc, A.; Crzela, T.; and Malejczyk, J., "Differences in Cartilage Formed Intramuscularly or in Joint Surface Defects by Syngeneic Rat Chondrocytes Isolated from the Articular–Epiphyseal Cartilage Complex," Cell Transplantation, vol. 2, 1993, pp. 467–473.

Moskalewski, S. and Malejczyk, J., "Bone formation following intrarenal transplantation obsolated murine chondrocytes: chondrocyte—bone cell transdifferentiation?", Development, vol. 107, 1989, pp. 473–480.

Moskalewski, S.; Malekszyk, J.; and Osiecka, A., "Structural Differences Between Bone Formed Intramuscularly Following the Transplantation of Isolated Calvarial Bone Cells or Chondrocytes," Anat. Embrol, vol. 175, 1986, pp. 271–277.

Moskalewski, S., "The Elastogenetic Process in Transplants and Cultures of Isolated Auricular Chondrocytes," Connective Tissue Research, vol. 8, 1981, pp. 171–174.

Moskalewski, S. and Rybicka, E., "The influence of the degree of maturation of donor tissue on the reconstruction of elastic cartilage by isolated chondrocytes," Acta anat., vol. 97, 1977, pp. 231–240.

Mutter, D., et al., Biomaterial Supports for Colonic Wall Defect Healing, Biomaterials, 1996, 17:1411–1415.

Nehrer, Stefan; Breinan, Howard, A.; Ramappa, Arun; Shortkroff, Sonya; Young, Gretchen; Minas, Tom; Sledge, Clement, B.; Yannas, Ioannis, V.; and Spector, Myron, "Canine Chondrocytes Seeded in Type I and Type II Collagen Implants Investigated In Vitro", Journal of Biomedical Materials Research, vol. 38, pp. 95–104, 1997.

Nixon, A.J., BVSc, MS; Sames, A.E., DVM; Lust, G., PhD; Grande, D.; PhD; and Mohammed, H.O., BVSc, PhD, "Temporal matrix synthesis and histologic features of chrondrocyte–laden porous collagen cartilage analogue," American Journal of Veterinary Research, vol. 54, No. 2, Feb. 1993, pp. 349–356.

Osiecka, A.; Malejczyk, J.; and Moskalewski, S., "Cartilage Transplants in Normal and Preimmunized Mice," Arch Immunol Ther Exp (Warsz), 1990, vol. 38(5–6), pp. 461–473.

Pachene, J., Collagen Based Devices for Soft–Tissue Repair, 1996, J. Biomed. Mater. Res., 33(1):35–40.

Perka, C.; Lindenhayn, K.; Heilmann, H.–H.; Sittinger, M.; and Muschlik, M., "Implantation of Allogenic Embryonal Chondrocytes in a Collagen–Fibrogen Matrix into Mechanical Induced Full–Thickness Defects of Chick Articular Cartilage," Z. Orthop., vol. 134, 1996, pp. 562–572. (Abstract in English).

Praemer, Allan, M.A.; Furner, Sylvia, Ph.D.; and Rice, Dorothy, P., "Muskuloskeletal Conditions in the United States, Section 4: Medical Implants and Major Joint Procedures", pp. 127–141, Academy of Orthopaedic Surgeons, Feb. 1992.

Quatela, Vito, C., M.D.; Sherris, David, A., M.D.; and Rosier, Randy, N., M.D., Ph.D., The Human Auricular Chondrocyte: Responses to Growth Factors, Arch Otolaryngol Head Neck Surg., vol. 119, Jan. 1993, pp. 32–27.

Reichenberger, E.; Aigner, T.; Von Der Mark, K.; Stob, H.; and Bertling W., "In Situ Hybridization Studies on the Expression of Type X Collagen in Fetal Human Cartilage," Development Biology, vol. 148, 1991, pp. 562–572.

Ronning, O. and Peltomaki, "Growth Potential of the Rat Mandibular Condyle as an Isogeneic Transplant Traversing the Interparietal Suture," Arcs oral Biol., vol. 36, No. 3, 1991, pp. 203–210.

Roth et al., "The Intrinsic Tensile Behavior of the Matrix of Bovine Articular Cartilage and Its Variation with Age", Journal of Bone and Joint Surgery, vol. 62, No. 7, Oct., 1980, pp. 1102–1117.

Sams, A., et al., Chondrocyte–laden Collagen Scaffolds for Resurfacing Extensive Articular Cartilage Defects, Osteoarthritis and Cartilage, 1995, 3:47–59.

Sams, A., et al., Local and Remote Matrix Responses to Chondrocyte–laden Collagen Scaffold Implantation in Extensive Articular Cartilage Defects, Osteoarthritis and Cartilage, 1995, 3:61–70.

Sittinger M. et al, "Engineering of Cartilage Tissue Using Bioresorbable Polymer Carriers In Perfusion Culture", Biomaterials, 1994, vol. 15, No. 6, p. 451–456.

Stephens, Myra; Kwan, Alvin, P. L.; Bayliss, Michael, T.; and Archer, Charles, W.; "Human articular surface chondrocytes initiate alkaline phosphatase and type X collagen synthesis in suspension culture," Journal of Cell Science, vol. 103, 1992, pp. 1111–1116.

Stone, et al., "Surgical Technique for Articular Cartilage Transplantation to Full–Thickness Cartilage Defects in the Knee Joint", Articular Cartilage Transplantation, p. 305–311 (1997).

Stone, Kevin, R., M.D.; Steadman, Richard, J., M.D., Rodkey, William, G., D.V.M.; and Li, Shu–Ting, Ph.D., "Regeneration of Meniscal Cartilage with Use of a Collagen Scaffold," The Journal of Bone and Joint Surgery, vol. 79–A, No. 12, Dec. 1997, pp. 1770–1777.

Stone, K., et al., Future Directions: Collagen–Based Prostheses for Meniscal Regeneration, Clinical Othopaedics and Related Research, 1990, 252:129–135.

Stone, K., et al., Meniscal Regeneration with Copolymeric Collagen Scaffolds, Am. J. Sports Med., 1992, 20(2):104–111.

Suh, et al., "Injury and Repair of Articular Cartilage: Related Scientific Issues", Operative Techniques on Orthopaedics, vol. 7, No. 4, Oct., 1997, pp. 270–278.

Toolan, et al., "Effects of Growth Factor–Enhanced Culture on a Chondrocyte–collagen Implant for Cartilage Repair," Journal of Biomedical Materials Research, 1996, vol. 31, pp. 273–280.

Van Susante, Job, L.; Buma, Pieter; Van Osch, Gerjo, J.V.M.; Versleyen, Diny; Van Der Kraan, Peter, M.; Van Der Berg, Wim, B.; and Homminga, Gerorge, N., "Culture of Chondrocytes in alginate and collagen carrier gels," Acta Orthop Scand, vol. 66, No. 6 (1995), pp. 549–556.

Wakitani, Shigeyuki; Kimura, Tomoatsu; Hirooka, Atsushi; Ochi, Takahiro; Yoneda, Minoru; Yasui, Hatsuo, Owaki, Hajime; and Ono Keiro, "Repair of Rabbit Articular Surfaces with Allograft Chondrocytes Embedded in Collagen Gel,", Journal of Bone and Joint Surgery, vol. 71–B, No. 1, pp. 74–80, Jan. 1989.

Wheater, Burkitt, and Daniels, "Chapter 4: Connective Tissue", 2nd Edition (Church livingstone, London 1987), pp. 52–63.

Wheater, Paul; Burkitt, George; Stevens, Alan; and Lowe, James, "Chapter 21: Skeletal system", Basic Histopathology—A Color Atlas and Text, Churchill Livingstone, 1985, pp. 195–200.

Woo, Savio L–Y.; Mow, Van C.; and Lai, W. Michael, Handbook of Bioengineering, Biomechanical Properties of Articular Cartilage, McGraw–Hill Book Company, 1987, Chapters 4 and 5.

Yoshinao, Masatoshi, "Immune Responses to Articular Cartilage Reconstruction Using Chondrocytes Allograft Transplant," J. Jpn. Orthop. Assoc., vol. 64, 1990, pp. 835–846. (Abstract in English).

* cited by examiner

METHODS, INSTRUMENTS AND MATERIALS FOR CHONDROCYTE CELL TRANSPLANTATION

This application is a continuation of U.S. patent application Ser. No. 09/373,952, filed Aug. 13, 1999 now abandoned . Further, the present invention relates to the field of chondrocyte cell transplantation, bone and cartilage grafting, healing, joint repair and the prevention of arthritic pathologies. In particular, the present invention is directed to new methods and instruments for chondrocyte cell transplantation and cartilage regeneration, as previously described in U.S. provisional patent application No. 60/096, 597, filed Aug. 14, 1998, and a U.S. provisional patent application No. 60/146,683, filed Aug. 2, 1999, both of which are hereby incorporated by reference.

FIELD OF THE INVENTION

BACKGROUND OF THE INVENTION

More than 500,000 arthroplastic procedures and total joint replacements are performed each year in the United States. Approximately the same number of similar procedures are performed in Europe. Included in this number in Europe are about 90,000 total knee replacements and around 50,000 procedures to repair defects in the knee. These numbers are essentially the same in the U.S. (Praemer A., Furner S., Rice, D. P., Musculoskeletal conditions in the United States, American Academy of Orthopaedic Surgeons, Park Ridge, Ill., 1992, 125).

A method for regeneration-treatment of cartilage would be most useful and could be performed at an earlier stage of joint damage, thus reducing the number of patients needing artificial joint replacement surgery. With such preventive methods of treatment, the number of patients developing osteoarthritis would also decrease.

Techniques used for resurfacing the cartilage structure in joints have mainly attempted to induce the repair of cartilage using subchondral drilling, abrasion and other methods whereby there is excision of diseased cartilage and subchondral bone, leaving vascularized cancerous bone exposed (Insall, J., Clin, Orthop. 1974, 101, 61; Ficat R. P. et al., Clin. Orthop. 1979, 144, 74; Johnson L. L., in *Operative Arthroscopy*, McGinty J. B., Ed., Raven Press, New York, 1991, 341).

Coon and Cahn (Science 1966, 153, 1116) described a technique for the cultivation of cartilage synthesizing cells from chick embryo somites. Later, Cahn and Lasher (PNAS USA 1967, 58, 1131) used the system for analysis of the involvement of DNA synthesis as a prerequisite for cartilage differentiation. Chondrocyte cells respond to both EFG and FGF by growth (Gospodarowicz and Mescher, J. Cell Physiology) 1977, 93, 117), but ultimately lose their differentiated function (Benya et al., Cell 1978, 15, 1313). Methods for growing chondrocyte cells were described and are principally being used with minor adjustments by Brittberg, M. et al. (new Engl. J. Med. 1994, 331, 889). Cells grown using these methods were used as autologous transplants into knee joints of patients. Additionally, Kolettas et al. (J. Cell Science 1995, 108, 1991) examined the expression of cartilage-specific molecules such as collagens and proteoglycans under prolonged cell culturing. They found that despite morphological changes during culturing in monolayer cultures (Aulthouse, A. et al., In vitro Cell Dev. Biol., 1989, 25, 659; Archer, C. et al., J. Cell Sci. 1990, 97, 361; Hänselmann, H. et al., J. Cell Sci. 1994, 107, 17; Bonaventure, J. et al., Exp. Cell Res. 1994, 212, 97), when compared to suspension cultures grown over agarose gels, alginate beads or as spinner cultures (retaining a round cell morphology) tested by various scientists did not change the chondrocyte—expressed markers such as types II and IX collagens and the large aggregating proteoglycans, aggrecan, versican and link protein did not change (Kolettas, E. et al., J. Cell Science 1995, 108, 1991).

Wakitani et al. (Tissue Engineering 4 (4),429 (1989) described the use of collagen Type I gels in animal experiments to repair cartilage defects. In all instances, the major problem was the lack of biomechanical properties required for functional tissue repair.

The articular chondrocytes are specialized mesenchymal derived cells found exclusively in cartilage. Cartilage is an avascular tissue whose physical properties depend on the extracellular matrix produced by the chondrocytes. During endochondral ossification, chondrocytes undergo a maturation leading to cellular hypertrophy, characterized by the onset of expression of type X collagen (Upholt, W. B. and Olsen, R. R., In: Cartilage *Molecular Aspects* (Hall, B. & Newman, S., Eds.) CRC Boca Raton 1991, 43; Reichenberger, E. et al., Dev. Biol. 1991, 148, 562; Kirsch, T. et al., Differentiation, 1992, 52, 89; Stephens, M. et al., J. Cell Sci. 1993, 103, 1111).

Excessive degradation of type II collagen in the outer layers of articular surfaces of joints is also caused by osteoarthritis. The collagen network is accordingly weakened and subsequently develops fibrillation whereby matrix substances such as proteoglycans are lost and eventually displaced entirely. Such fibrillation of weakened osteoarthritis cartilage can reach down to the calcified cartilage and into the subchondral bone (Kempson, G. E. et al., Biochem. Biophys. Acta 1976, 428, 741; Roth, V. and Mow, V. C., J. Bone Joint Surgery, 1980, 62A, 1102; Woo, S. L.-Y. et al., in *Handbook of Bioengineering* (R. Skalak and S. Chien Eds), McGraw-Hill, New York, 1987, pp. 4.1–4.44).

Descriptions of the basic development, histological and microscopic anatomy of bone, cartilage and other such connective tissues can be found for example in Wheater, Burkitt and Daniels, *Functional Histology*, $2^{nd}$ Edition (Churchill Livingstone, London 1987, Chp. 4). Descriptions of the basic histological anatomy of defects in bone, cartilage and other connective tissue also can be found for example in Wheater, Burkitt, Stevens and Lowe, *Basic Histopathology*, (Churchill Livingstone, London, 1985, Chp. 21).

Although the need for chondrocyte cell transplantation has been described at length at least in the above mentioned references, there remains a need for a satisfactory and effective procedure for cartilage repair either by transplantation or otherwise.

BRIEF SUMMARY OF THE INVENTION

The present invention provides an implantable article including a support matrix which can support the growth and attachment of cells thereto, and a method of implanting such an article to regenerate cells at an implantation location. In one embodiment, the present invention provides a method for the effective treatment of articulating joint surface cartilage in an animal by the transplantation of an implantable article including chondrocyte cells retained on an absorbable support matrix. In one embodiment, the support matrix is made from collagen such as Type I or Type II collagen, and the chondrocyte cells are autologous or homologous. The implantable article preferably is secured to the transplantation site by an adhesive or mechanical retention means. The present invention also is directed to an instrument for placing and manipulating the implantable article at the site of implantation, and a retention device for securing the implantable article to the site of implantation.

The present invention is also directed to an implantable article for cartilage repair in an animal, the implantable article including chondrocyte cells retained to an absorbable support matrix, and a method of making same.

BRIEF DESCRIPTION OF THE DRAWINGS

The present invention may be better understood by reference to the description which follows taken together with the accompanying figures which illustrate the present invention wherein:

FIG. 11AA is the color microphotograph of FIG. 11A.

FIG. 11BB is the color microphotograph of FIG. 11B.

DETAILED DESCRIPTION OF THE INVENTION

Figure 1A:
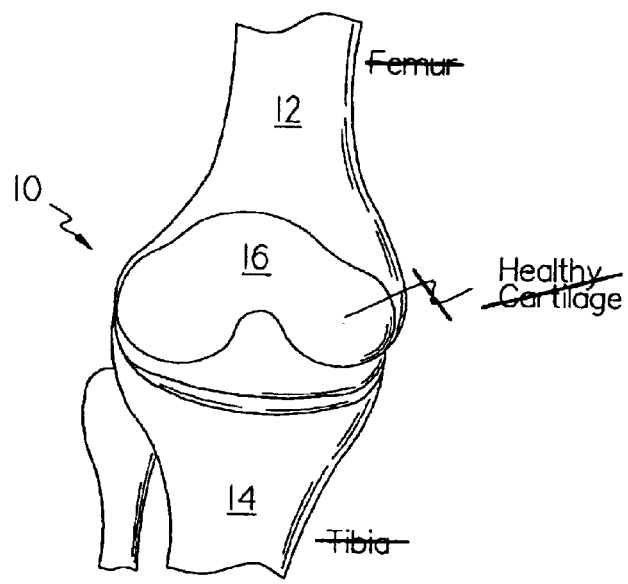
FIG. 1A shows a typical articulating end of a bone in a knee joint, having an articulating surface with a cartilaginous cap.
Figure 1B:
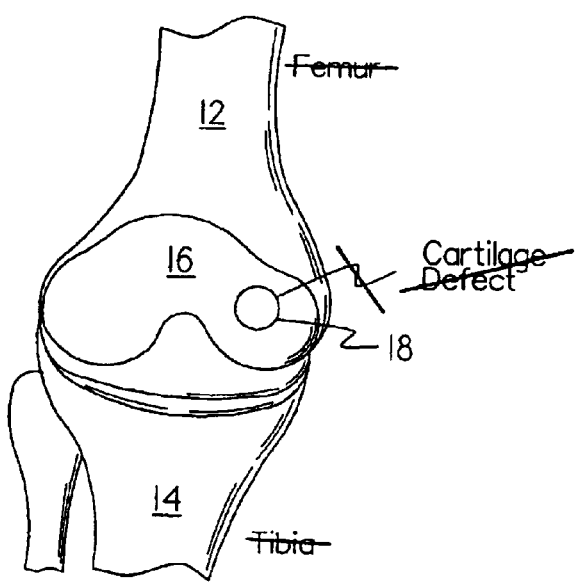
FIG. 1B shows a cartilage defect or injury to a cartilaginous cap of an articulating end of a bone.

As discussed above, one joint of the human body where cartilage damage and defects often occur is the knee. FIG. 1A shows a typical articulating end of a bone in a human knee joint 10. Knee joint 10 is formed by the juncture of femur 12 and tibia 14, and healthy cartilage 16 covering the articulating end of femur 12. FIG. 1B shows a circular area of defect or injury 18 (hereinafter sometimes defect 18) in cartilage 16.

The present invention includes a cartilage repair implant and implantation method and apparatus for such an implant. The implant comprises a support matrix and autologous or homologous chondrocyte cells retained thereon. Generally, the support matrix is a material which will support chondrocyte cell growth and which, over time will be absorbed in a body of a patient receiving the implant. The transplantation procedure may be by arthroscopic, minimally invasive or open surgery technique. The method of the invention also contemplates the use of suitable allogenic and xenogenic chondrocyte cells for the repair of a cartilage defect.

Figure 2:
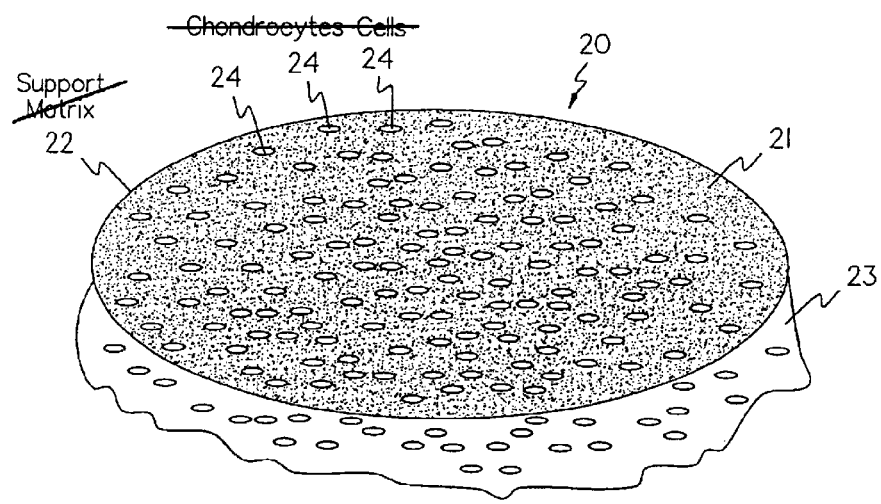
FIG. 2 shows one embodiment of an implantable article according to the present invention.

FIG. 2 shows such an implant. More specifically, an implantable article 20 includes a support matrix 22 having chondrocyte cells 24 retained thereon. A suitable support matrix 22 will be a solid or gel-like, scaffold characterized by being able to hold a stable form for a period of time to enable the growth of chondrocytes cells thereon, both before transplant and after transplant, and to provide a system similar to the natural environment of the chondrocyte cells to optimize chondrocyte cell growth differentiation.

Support matrix 22 will be stable for a period of time sufficient to allow full cartilage repair and then be absorbed by the body over time, for example, within two to three months without leaving any significant traces and without forming toxic degradation products. The term "absorbed" is meant to include processes by which the support matrix is broken down by natural biological processes, and the broken down support matrix and degradation products thereof are disposed of, for example, through the lymphatics or blood vessels. Accordingly, support matrix 22 preferably is a physiologically absorbable, non-antigenic membrane-like material. Further, support matrix 22 preferably is in a sheet like form having one relatively smooth side 21 and one relatively rough side 23. Rough side 23, for example, is fibrous and typically faces cartilage defect 18 and promotes chondrocyte cell ingrowth, while the smooth side 21 typically faces away from cartilage defect 18 and impedes tissue ingrowth.

In one embodiment, support matrix 22 is formed of polypeptides or proteins. Preferably, the polypeptides or proteins are obtained from natural sources, e.g., from mammals. Artificial materials, however, having physical and chemical properties comparable to polypeptides or proteins from natural sources, may also be used to form support matrix 22. It is also preferred that support matrix 22 is reversibly deformable as it is handled by the user so implantable article 20 can be manipulated and then returns to its original shape as described below, during one aspect of the present invention.

A preferred material from which support matrix 22 can be formed is collagen such as obtained from equine, porcine, bovine, ovine, and chicken. Suitable materials from which support matrix 22 can be formed include Chondro-Cell® (a commercially available type II collagen matrix pad, Ed. Geistlich Söhne, Switzerland), and Chondro-Gide® (a commercially available type I collagen matrix pad, Ed. Geistlich Söhne, Switzerland). A support matrix 22 formed of collagen Type I is somewhat stiffer than a support matrix formed from collagen Type II, although Type II collagen matrixes may also be used.

An implantable article as described above may be made, for example, by culturing chondrocyte cells on this support matrix as described in more detail below.

For an autologous implant, a cartilage biopsy first is harvested by arthroscopic technique from a non-weight bearing area in a joint of the patient and transported to the laboratory in a growth media containing 20% fetal calf serum. The cartilage biopsy is then treated with an enzyme such as trypsin ethylenediaminetetraacetic acid (EDTA), a proteolytic enzyme and binding agent, to isolate and extract cartilage chondrocyte cells. The extracted chondrocyte cells are then cultured in the growth media from an initial cell count of about 50,000 cells to a final count of about 20 million chondrocyte cells or more.

Three (3) days before reimplantation, the growth media is exchanged for a transplant media which contains 10% autologous serum (that is, serum extracted from the patient's blood as described below). Then, the cultured chondrocyte cells in the transplant media are soaked into and penetrate support matrix 22, and continue multiplying to form implantable article 22. Implantable article 22 is then implanted at a site of cartilage defect 18 in the patient.

It is understood that defect or injury 18 can be treated directly, enlarged slightly, or sculpted by surgical procedure prior to implant, to accommodate implantable article 20. The culturing procedure as well as the growth and transplant medias are described by way of example, in detail below, starting first with a description of a laboratory procedure used to process the harvested cartilage biopsy and to culture the chondrocyte cells according to the present invention.

Growth media (hereinafter, "the growth media") used to treat the cartilage biopsy during the culturing process and to grow the cartilage chondrocyte cells is prepared by mixing together 2.5 ml gentomycin suflate (concentration 70 micromole/liter), 4.0 ml amphotericin (concentration 2.2 micromole/liter; tradename Fungizone®, an antifungal available from Squibb), 15 ml 1-ascorbic acid (300 micromole/liter), 100 ml fetal calf serum (final concentration 20%), and the remainder DMEM/F12 media to produce about 400 ml of growth media. (The same growth media is also used to transport the cartilage biopsy from the hospital to the laboratory in which the chondrocyte cells are extracted and multiplied.)

Blood obtained from the patient is centrifuged at approximately 3,000 rpm to separate the blood serum from other blood constituents. The separated blood serum is saved and used at a later stage of the culturing process and transplant procedure.

Cartilage biopsy previously harvested from a patient for autologous transplantation is shipped in the growth media described above to the laboratory where it will be cultured. The growth media is decanted to separate out the cartilage biopsy, and discarded upon arrival at the laboratory. The cartilage biopsy is then washed in plain DMEM/F12 at least three times to remove the film of fetal calf serum on the cartilage biopsy.

The cartilage biopsy is then washed in a composition which includes the growth media described above, to which 28 ml trypsin EDTA (concentration 0.055) has been added. In this composition it is incubated for five to ten minutes at 37° C., and 5% $CO_2$. After incubation, the cartilage biopsy is washed two to three times in the growth media, to cleanse the biopsy of any of the trypsin enzyme. The cartilage is then weighed. Typically, the minimum amount of cartilage required to grow cartilage chondrocyte cells is about 80–100 mg. A somewhat larger amount, such as 200 to 300 mg, is preferred. After weighing, the cartilage is placed in a mixture of 2 ml collagenase (conentration 5,000 enzymatic units; a digestive enzyme) in approximately 50 ml plain DMEM/F12 media, and minced to allow the enzyme to partially digest the cartilage. After mincing, the minced cartilage is transferred into a bottle using a funnel, and approximately 50 ml of the collagenase and plain DMEM/F12 mixture is added to the bottle. The minced cartilage is then incubated for 17 to 21 hours at 37° C., and 5% $CO_2$.

In one embodiment, the incubated minced cartilage is then strained using 40 μm mesh, centrifuged (at 1054 rpm, or 200 times gravity) for 10 minutes, and washed twice with growth media. The chondrocyte cells are then counted to determine their viability, following which the chondrocyte cells are incubated in the growth media for at least two weeks at 37° C., and 5% $CO_2$, during which time the growth media was changed three to four times.

At least three days before re-implantation in the patient, the chondrocyte cells are removed by trypsinization and centrifugation from the growth media, and transferred to a transplant media containing 1.25 ml gentomycin sulfate (concentration 70 micromole/liter), 2.0 ml amphotericin (concentration 2.2 micromole/liter; tradename Fungizone®, an antifungal available from Squibb), 7.5 ml 1-ascorbic acid (300 micromole/liter), 25 ml autologous blood serum (final concentration 10%), and the remainder DMEM/F12 media to produce about 300 ml of transplant media.

Support matrix 22 is then cut to a suitable size fitting into the bottom of a well in a NUNCLON™ cell culture tray, and then placed under aseptic conditions on the bottom of the well with 1–2 ml transplant media. A sufficient number of cultivated cartilage chondrocyte cells (e.g. 3–10 million chondrocyte cells) in approximately 5–10 ml of the transplant media, are then soaked into support matrix 22, and incubated approximately 72 hours at 37° C., and 5% $CO_2$ to allow the chondrocyte cells to continue to grow. During this incubation, the chondrocyte cells arrange in clusters and adhere to support matrix 22. Using this method, it has been found that support matrix 22 supports the growth and retention of chondrocyte cells thereon in a sufficient number to form implantable article 20, without significant loss of the biomechanical properties of support matrix 22. Support matrix 22 also provides an environment to support continued growth of chondrocyte cells after implantation of the implantable article at the site of cartilage defect.

In another embodiment, following the 17–21 hour incubation period and after determining cell count and viability as discussed above, the chondrocyte cells are transferred to the transplant media and then grown directly on support matrix 22 for a period of at least two weeks.

It has been found that implantable article 20 temporarily can be deformed without mechanical destruction or loss of the chondrocyte cells adhered to support matrix 22. This deformation is completely reversible once implantable article 20 is introduced into the joint or is placed on the surface to be treated, as described below.

Accordingly, and in accordance with another aspect of the present invention, support matrix 22 onto which chondrocyte cells are grown or loaded in a sufficient number, temporarily can be deformed in a way that allows its introduction into the working device of an arthroscope without mechanical destruction or loss of its chondrocyte cell load.

At the same time it has been found that this matrix can be secured by adhesive or mechanical retention means, to the cartilage defect area without impairing the further in situ differentiation of the chondrocytes and the regeneration of the natural cartilage matrix material.

Other aspects of the present invention include instruments to place implantable article 20 at the implantation site, and a mechanical retention device to hold implantable article 20 at the implantation site.

Figure 3A:
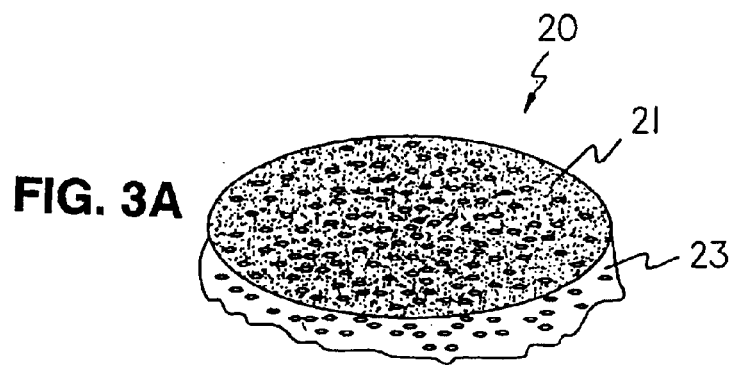
FIG. 3 shows how the implantable article of FIG. 2 may be disposed for implantation in an arthroscopic introducer such as that shown in FIG. 4.
Figure 3B:
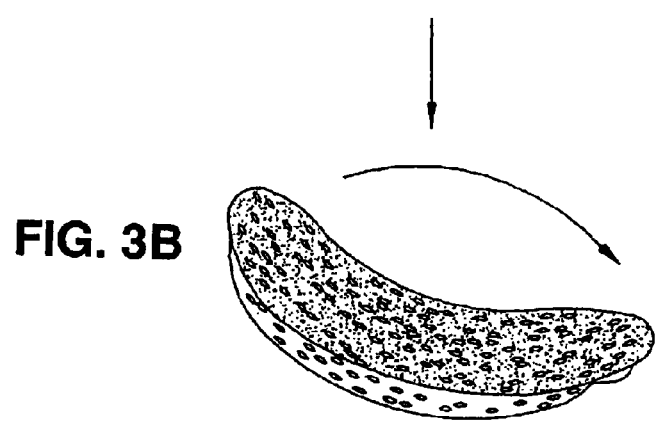
Figure 3C:
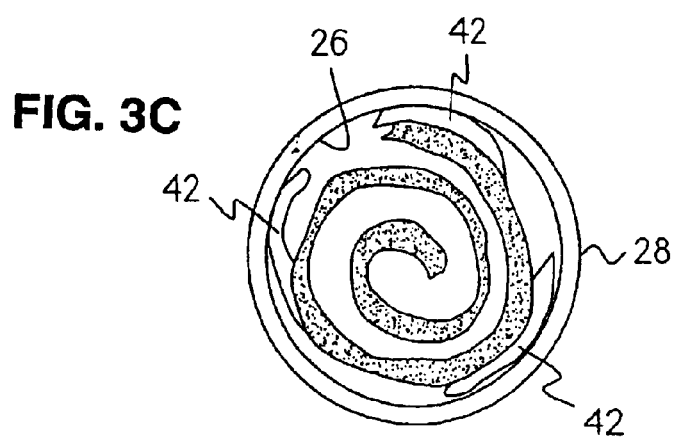

In one embodiment of the present invention, the implantation procedure is performed by an arthroscopic technique. FIG. 3 shows how implantable article 20 can be rolled across the diameter thereof to form a spirally would transplant cylindrical so that implantable article 20 can be delivered to an implantation site through a working channel 26 of an arthroscopic introducer 28. A suitable arthroscopic introducer is depicted in FIG. 4.

Figure 4:
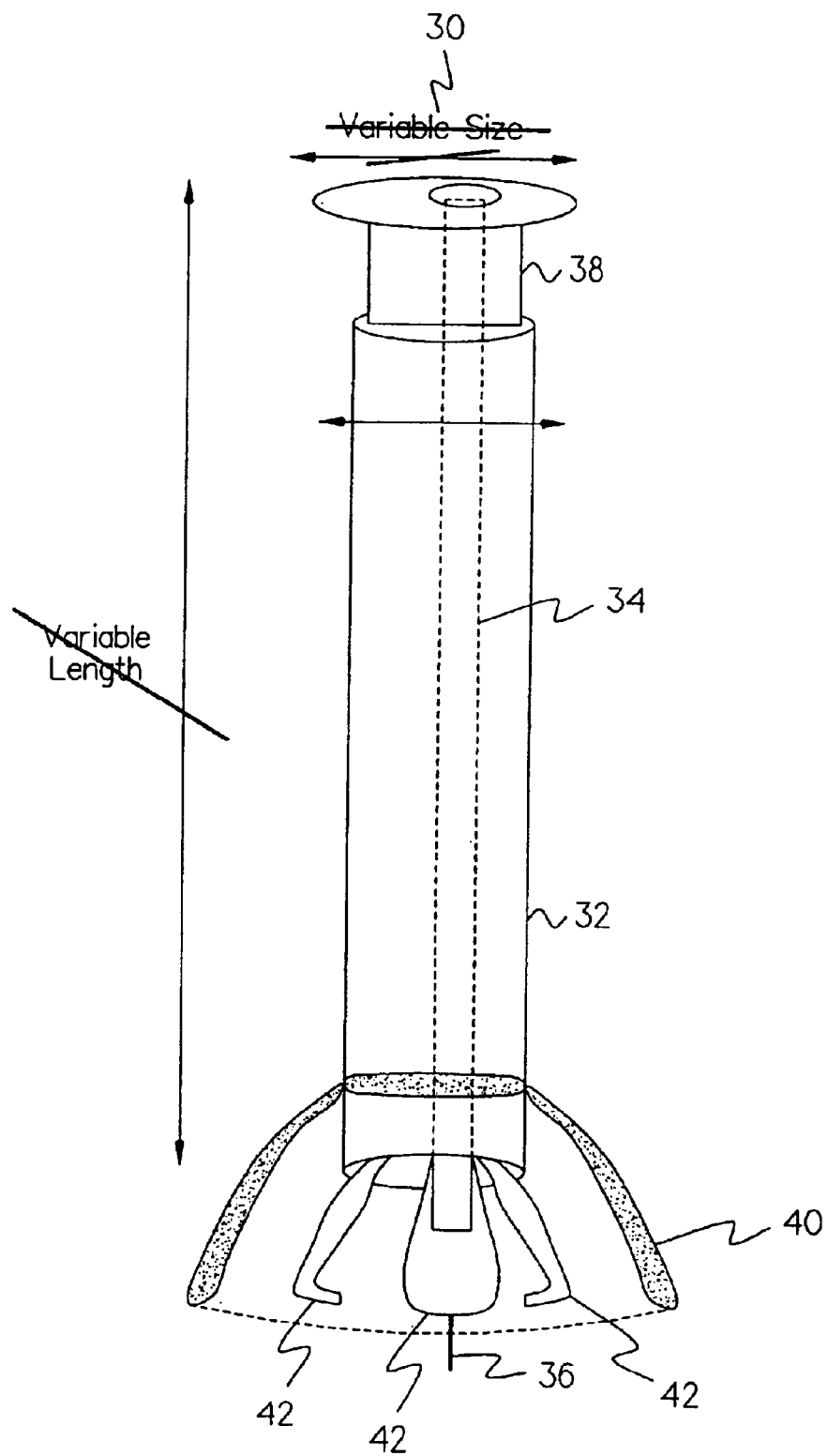
FIG. 4 shows an arthroscopic introducer for implanting the implantable article at the site of implantation, according to the present invention.

In FIG. 4, an arthroscopic introducer 30 includes a working channel 32 having a diameter and length suitable to enter the joint of interest and to deliver the desired dimension of implantable article 20. For example, for most procedures, the diameter of working channel 32 is approximately 8–20 mm, and the length is approximately 30–60 cm. Within and longitudinally movable with respect to working channel 32 is an injection channel 34 accommodating a retractable and removable needle 36. Injection channel 32 is attached to a handle 38 which is telescopically depressible at least partially into working channel 32. Needle 36 extends the length of injection channel 34 and allows fluids to pass therethrough to the site of implantation. Injection channel 34 is moved within working channel 32 by telescopically moving handle 38 toward or away from the implantation site.

Introducer 30 also includes a cap 40 made of rubber or other suitable material, slideably engaged on introducer 30. In use, cap 40 surrounds the site of cartilage defect and excludes fluids, such as blood and other natural fluids, from flowing into the site of cartilage defect. Introducer 30 also has two or more outwardly biased gripping elements 42 attached to handle 38, for grasping, introducing and placing implantable article 20 at the implantation site. In use, as handle 38 is telescopically moved toward and away from the user, gripping elements 42 engage the inside of working channel 32 and are moved toward each other in a gripping manner (as handle 38 is moved toward the user), and away from each other to release the grip (as handle 38 is moved away from the user). Such telescopic movement may be controlled by a biasing element (not shown) disposed within handle 38 which allows injection channel 34 and gripping elements 42 to be slideably advanced and retracted within working channel 42.

Figure 5A:
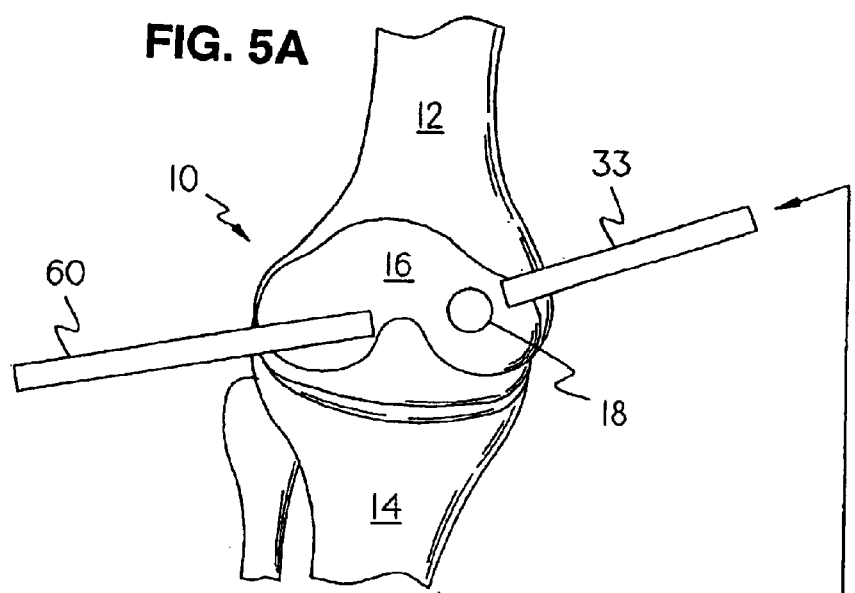
FIG. 5 is a drawing schematically illustrating the placement of the implantable article of FIG. 3 at the site of defect or injury in the cartilaginous cap using two access channels which can accommodate arthroscopic instruments.
Figure 5B:
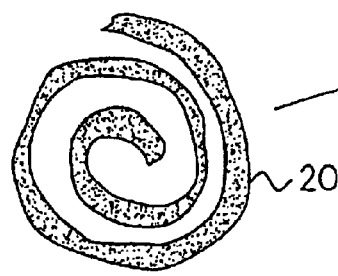
Figure 6:
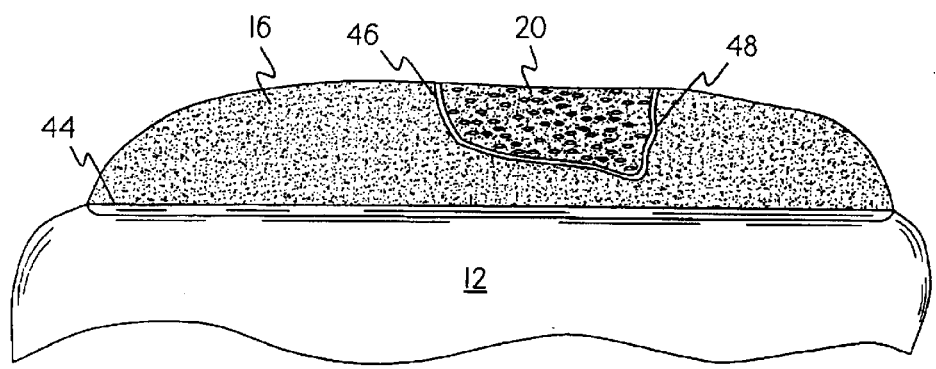
FIG. 6 is a schematic cross section of cartilage with a defect or injury which does not extend into the subchondral layer, and an implantable article according to the present invention secured by adhesive to the site of defect or injury.
Figure 7:
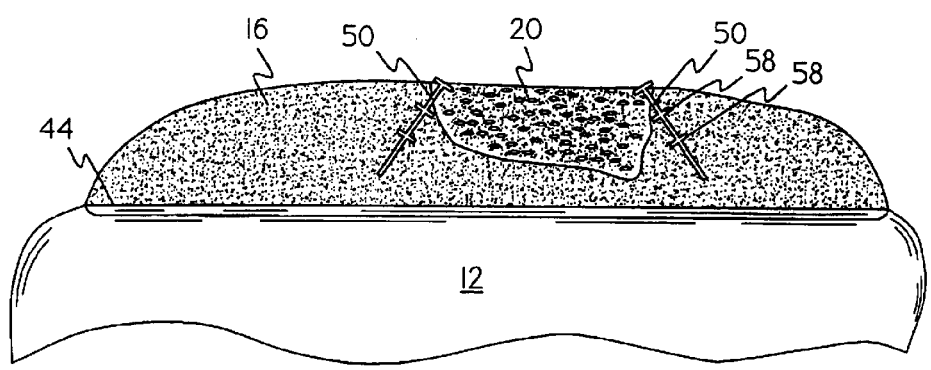
FIG. 7 is a schematic cross section of cartilage with a defect or injury which does not extend into the subchondral layer, and an implantable article secured to the site of defect or injury by a mechanical retainer.

FIGS. 5–7 show a typical arthroscopic procedure for implanting implantable article 22 at a site of implantation such as knee joint 10. Defective cartilage 18 is removed from the site of defect, preferably to a depth above subchondral layer 44 leaving a well 46 (See FIGS. 6–7). After cartilage defect 18 is removed, the defect site is prepared to receive implantable article 22. If the subchondral layer has been disturbed to the point that bleeding occurs at the implantation site, the site may first be covered with any absorbable material which acts as a hemostatic barrier.

Otherwise, site preparation may include injection of a biocompatible glue through needle 36 into well 46. Such a biocompatible glue, seen as adhesive 48 in FIG. 6, may comprise an organic fibrin glue (e.g., Tisseel®, fibrin based adhesive, Baxter, Austria or a fibrin glue prepared in the surgical theater using autologous blood samples).

Implantable article 20 previously cut to the desired dimension, and rolled into a spiral cylindrical shape as shown in FIG. 5 is then gripped by gripping elements 42 and held within the end of arthroscopic introducer 30. Arthroscopic introducer 30 holding implantable article 20 within its end, is then advanced to the site of implantation through an access channel 33, released from gripping elements 42, and unrolled using gripping elements 42 or allowed to unroll as it exits working channel 32. Access channel 33 includes one or more channels that allow instruments such as introducer 30 and visualization instruments, to access the transplantation site. Using gripping elements 42, implantable article 20 is manipulated such that rough side 23 of implantable article 20 faces well 46 and is gently held in place in well 46 to allow adhesive 48 to harden and bind implantable article 20 in well 46.

Figure 8:
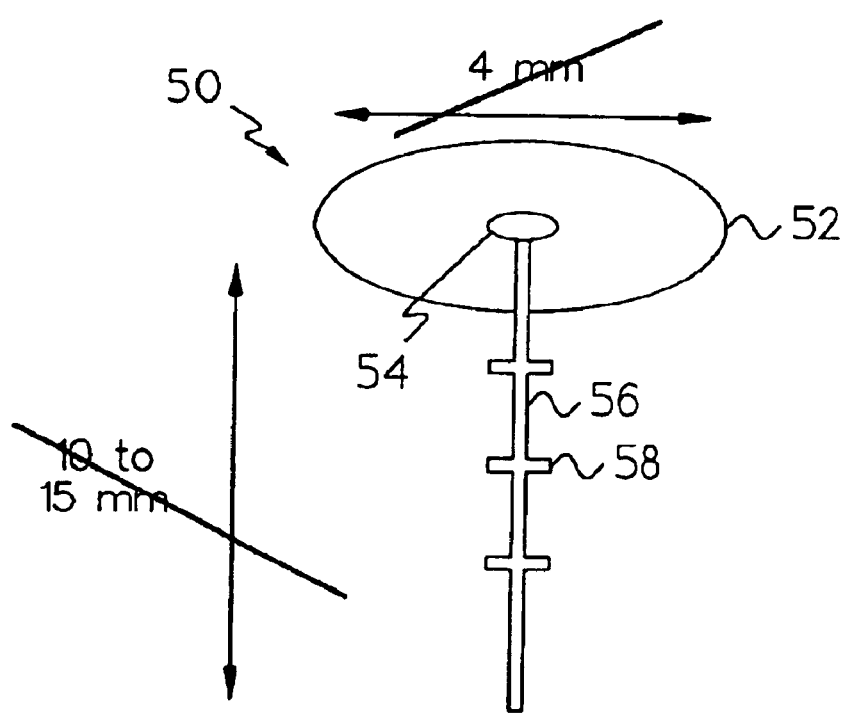
FIG. 8 illustrates one embodiment of the mechanical retainer used to secure the implantable article to the site of defect or injury.

In another embodiment (FIG. 7), mechanical retention means such as absorbable pins, anchors, screws or sutures are used to secure implantable article 20 in well 46. Suitable pins 50 include Ortho-Pin™ (a commercially available lactide co-polymer polymer pin, Ed. Geistlich Söhne, Switzerland). FIG. 8 shows one embodiment of absorbable pin 50. In this embodiment, pin 50 includes head 52, intramedullar channel 54 within shaft 56, and one or more retention rings 58. The dimensions of pin 50 will vary with the particular use, but, typically, pin 50 is about 10–15 mm in length, head 52 is about 4 mm in diameter, intramedullar channel 54 is approximately 1.2 mm in diameter, shaft 56 is approximately 2 mm in diameter, and retention rings 58 are about 2.5 mm in diameter. Retention rings 58 serve to anchor pin 50 into healthy cartilage surrounding the cartilage defect. Pin 50 is formed from any material that will not harm the body and can be absorbed or otherwise broken down by the body after a period of time. For example, pin 50 may be made from polylactide.

It is also contemplated to be within the scope of the present invention to use a combination of adhesive 48 and mechanical retention means such as pins 50 to secure implantable article 20 in well 46.

As shown in FIG. 6, a second access channel having one or more channels may be used to allow access of instruments to the site of implantation to assist in placement of the implantable article, adhesive and/or mechanical retention means, or to allow for access or visualization instruments to the site of implantation. Such a separate access channel may also be used to perform one or more of the functions described in relation to arthroscopic introducer 30 or other arthroscopic instruments.

Figure 9:
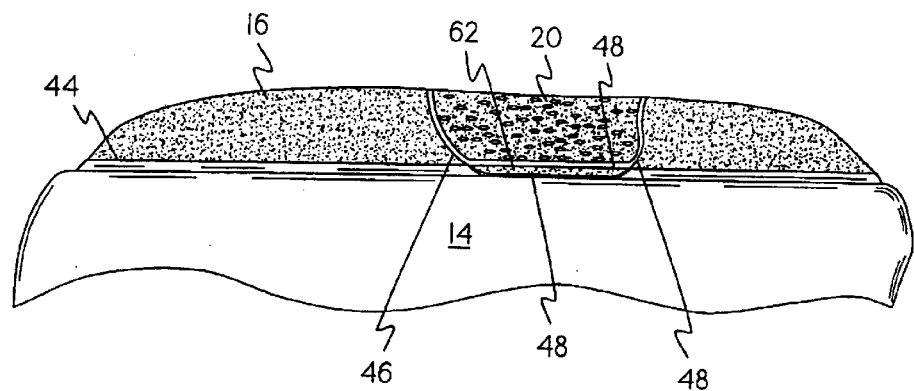
FIG. 9 is a schematic cross section of cartilage with a defect or injury which extends into the subchondral layer, and an implantable article according to the present invention secured by adhesive to the site of defect or injury.
Figure 10:
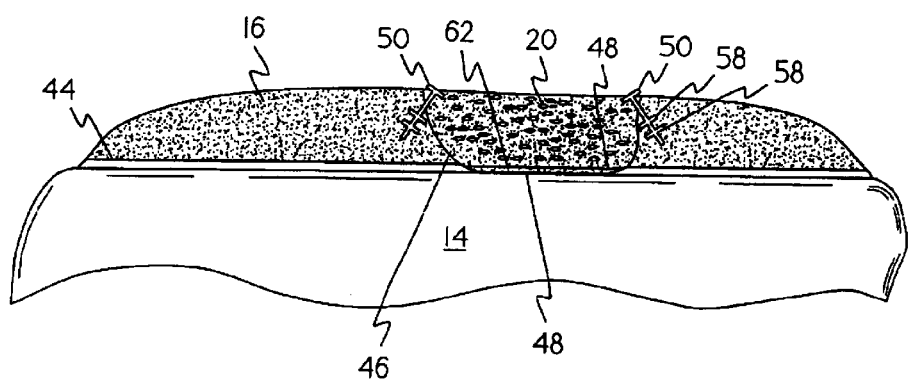
FIG. 10 is a schematic cross section of cartilage with a defect or injury which extends into the subchondral layer, and an implantable article secured to the site of defect or injury by a mechanical retainer.

As indicated above, where cartilage defect 18 extends into or below subchondral layer 44, or requires removal of cartilage into or below subchondral layer 44 as shown in FIGS. 9 and 10, the above procedure is modified to include placement of a hemostatic barrier 62 in well 46 prior to placement of implantable article 20. Hemostatic barrier 62 inhibits the growth or invasion of vascular tissue, osteocytes, fibroplasts, etc. into developing cartilage. This is believed to allow hyaline cartilage to grow at the transplantation site. Suitable hemostatic barriers will inhibit vascularization and cellular invasion into the developing cartilage to optimize formation of cartilage and to achieve growth of the full thickness of cartilage at the defect site. Preferably, the hemostatic barrier is stable for an extended period of time to allow full cartilage repair, and then will be absorbed or otherwise broken down by the body over time. A suitable hemostatic barrier is Surgicel® W1912 (Ethicon, Ltd., United Kingdom), an absorbable hemostat formed of oxidized regenerated sterile cellulose.

The above described surgical instruments are manufactured from any material, such as metal and/or plastic or silicone, suitable for making disposable or multi-use reusable surgical instruments.

Certain aspects of the invention have been exemplified by using an in vitro system to study the behavior of chondrocyte cells when in contact with different support matrices. This in vitro testing predicts the ability of certain materials to mechanically withstand the arthroscopic procedure and also provides information as to chondrocyte cell growing behavior.

These and other aspects of the instant invention may be better understood from the following examples, which are meant to illustrate but not to limit the present invention.

EXAMPLE 1

Chondrocyte cells were grown for three weeks in the growth media described above in a $CO_2$ incubator at 37° C. and handled in a Class 100 laboratory at Verigen Transplantation Service ApS, Copenhagen, DK or at University of Lübeck, Lübeck, Germany. [Note that other compositions of growth media may also be used for culturing the chondrocyte cells.] The cells were trypsinised using trypsin EDTA for 5 to 10 minutes and counted using Trypan Blue viability staining in a Bürker-Türk chamber. The cell count was adjusted to $7.5 \times 10^5$ chondrocyte cells per milliliter. One NUNCLON™ plate was uncovered in the Class 100 laboratory.

A support matrix material, specifically a Chondro-Gide® collagen membrane, was cut to a suitable size to fit into the bottom of a well in a NUNCLON™ cell culture tray. In this case a circle of a size of approximately 4 cm was placed under aseptic conditions on the bottom of the well.

After three weeks, chondrocyte cells were transferred from the growth media to the transplant media described above, and approximately $5 \times 10^6$ chondrocyte cells in 5 ml transplant media were placed directly on top of the support matrix and dispersed over the surface thereof. The plate was incubated in a $CO_2$ incubator at 37° C. for 3 days. After this period the chondrocyte cells had arranged in clusters and started to grow on the support matrix, and could not be removed from the support matrix by rinsing it with medium or even by mechanically exerting mild pressure on the matrix.

Figure 11A:
FIG. 11A is a black and white copy of a color microphotograph of histological specimen of a solid support matrix at the beginning of chondrocyte cell growth thereon.
Figure 11A:
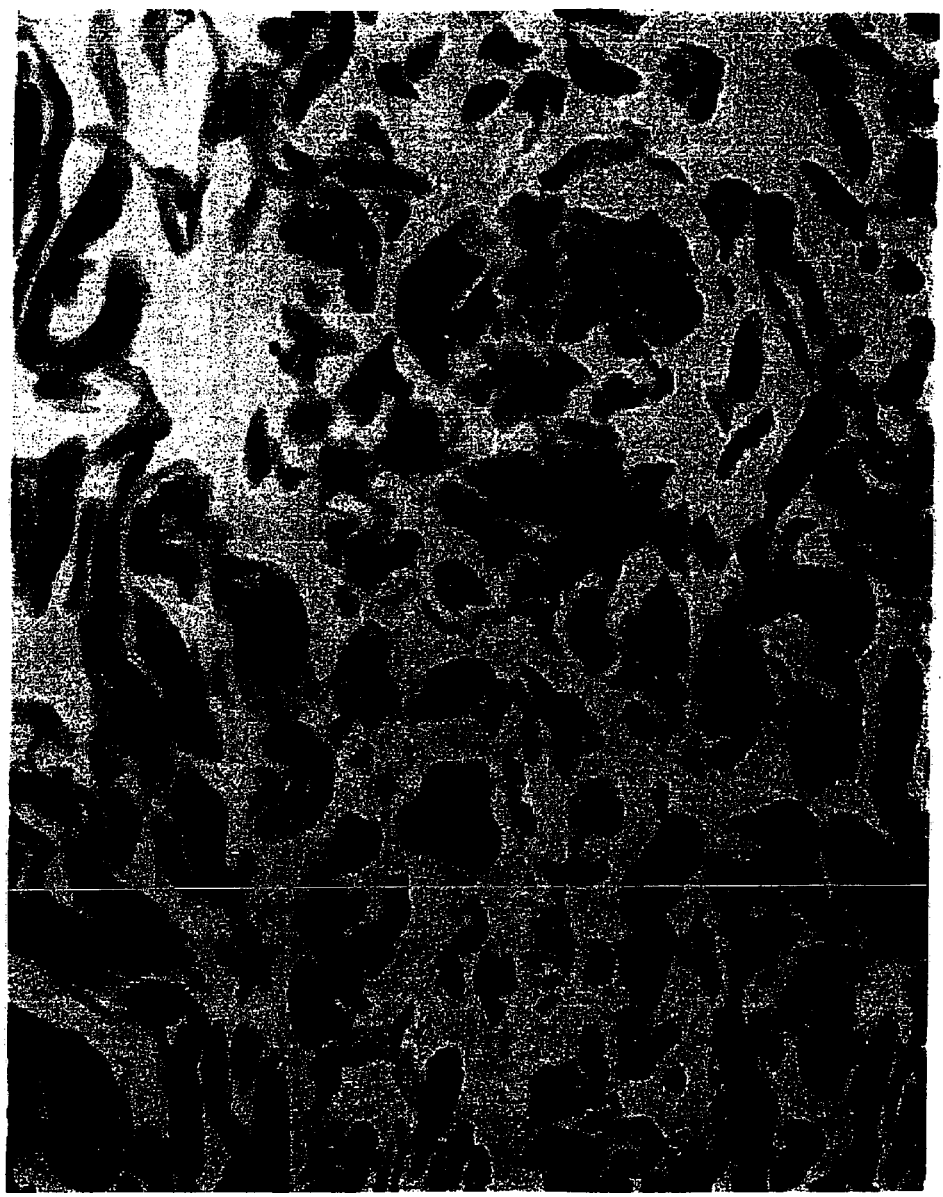

At the end of the incubation period, the transplant media was decanted and the support matrix holding chondrocyte cells grown thereon was cold refrigerated in 2.5% glutaraldehyde containing 0.1 M sodium salt of dimethylarsinic acid, added as fixative. The support matrix was stained with Safranin O for histological evaluation. A black and white copy of a color microphotograph thereof is shown in FIG. 11A. A color version of the microphotograph is also submitted as FIG. 11AA to better illustrate the features of the microphotograph.

EXAMPLE 2

Chondrocytes were grown for three weeks in the growth media described above in a $CO_2$ incubator at 37° C. and handled in a Class 100 laboratory at Verigen Transplantation Service ApS, Copenhagen, DK or at University of Lübeck, Germany. The cells were trypsinised using trypsin EDTA for 5 to 10 minutes and counted using Trypan Blue viability staining in a Bürker-Türk chamber. The chondrocyte cell count was adjusted to $5 \times 10^5$ chondrocyte cells per milliliter. One NUNCLON™ plate was uncovered in the Class 100 laboratory.

The Chondro-Gide® support matrix, as in Example 1, was cut to a suitable size fitting into the bottom of a well in the NUNCLON™ cell culture tray. In this case a circle of approximately 4 cm in diameter was placed under aseptic conditions on the bottom of the well.

After three weeks, the chondrocyte cells were transferred from the growth media to the transplant media described above, and approximately $5 \times 10^5$ cells in 5 ml transplant media were placed directly on top of the support matrix and dispersed over the surface of the support matrix. The plate was incubated in a $CO_2$ incubator at 37° C. for 3 weeks.

Figure 11B:
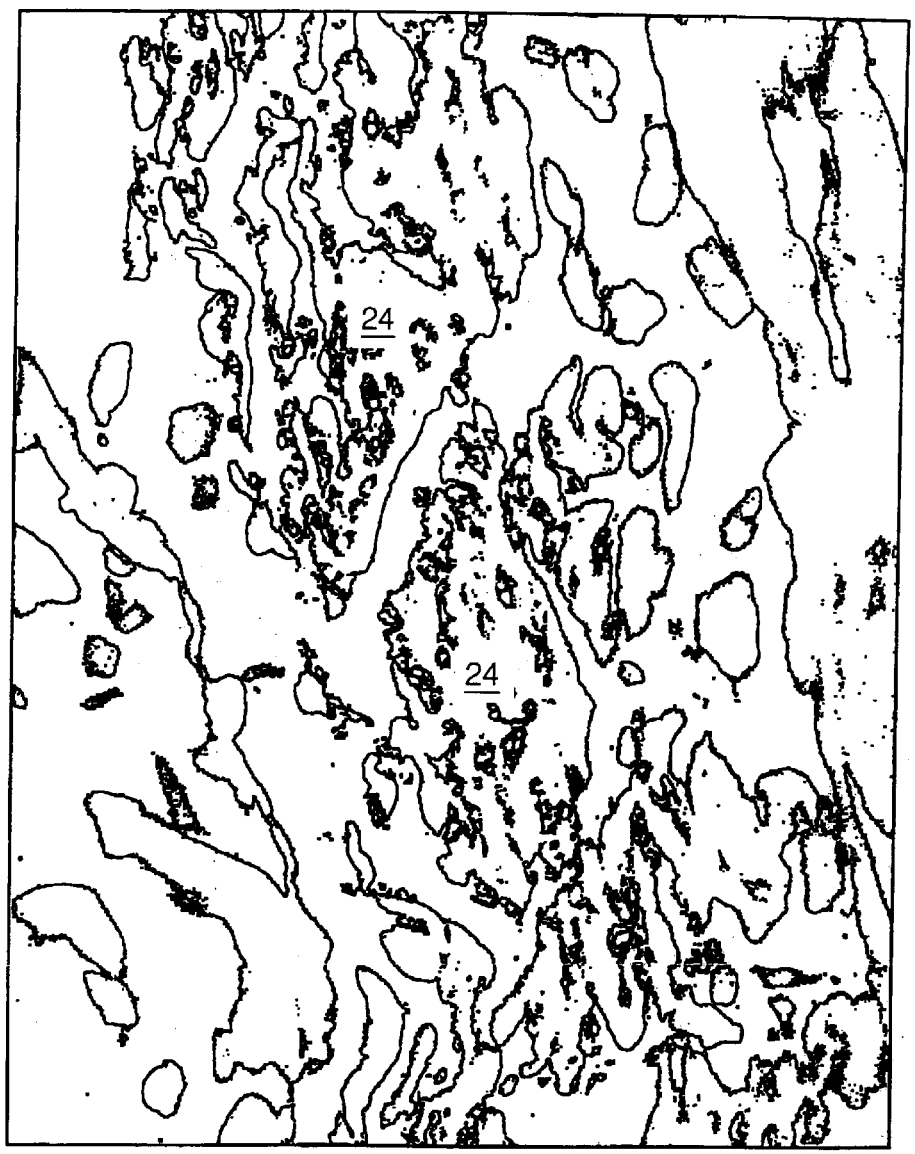
FIG. 11B is a black and white copy of a color microphotograph showing the support matrix of FIG. 11A loaded with chondrocyte cells after three weeks of chondrocyte cell growth thereon.
Figure 11B:
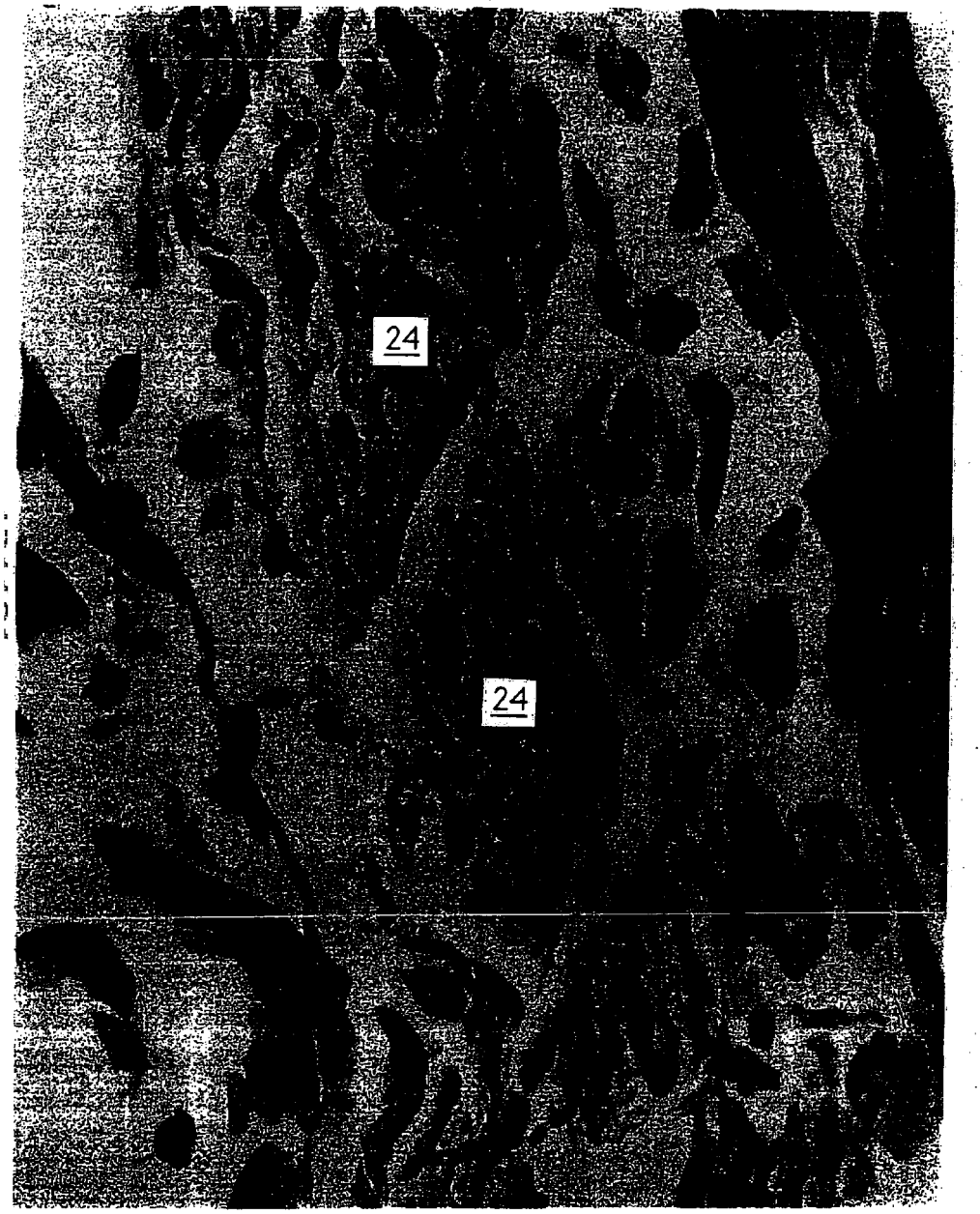

At the end of the incubation period, the transplant media was decanted, and the support matrix holding the chondrocyte cells thereon was cold refrigerated in 2.5% glutaraldehyde containing 0.1 M sodium salt of dimethylarsinic acid, added as fixative. The support matrix was stained with Safranin O for histological evaluation. For immunohistochemistry, collagene membranes were fixed in methanol-acetone and stained for aggrecane and Type II collagen using rabbit anti-human type II collagen and mouse anti-humane aggrecane. Primary antibodies were visualized using fluorescent secondary antibodies. A black and white copy of a color microphotograph thereof is shown in FIG. 11B showing chondrocyte cells 24. The color version is also submitted as FIG. 11BB to better illustrate the features of the microphotograph.

During the three week incubation period on the Chondro-Gide® support matrix, the chondrocyte cells were observed to have grown and multiplied on the support matrix building clusters in the center of the carrier and lining up along the surface.

EXAMPLE 3

Chondrocytes were grown for three weeks in the growth media described above in a $CO_2$ incubator at 37° C. and handled in a Class 100 laboratory at Verigen Transplantation Service ApS, Copenhagen, DK or at University of Lübeck, Germany. The chondrocyte cells were trypsinised using trypsin EDTA for 5 to 10 minutes and counted using Trypan Blue viability staining in a Bürker-Türk chamber. The chondrocyte cell count was adjusted to $5 \times 10^5$ chondrocyte cells per milliliter. One NUNCLON™ plate was uncovered in the Class 100 laboratory.

The Chondro-Gide® support matrix, as in Example 1, was cut to a suitable size fitting into the bottom of a well in the NUNCLON™ cell culture tray. In this case a circle of approximately 4 cm in diameter was placed under aseptic conditions on the bottom of the well.

After three weeks, the chondrocyte cells were transferred from the growth media to the transplant media described above, and approximately $5 \times 10^6$ cells in 5 ml transplant media were placed directly on top of the support matrix and dispersed over the surface of the support matrix. The plate was incubated in a $CO_2$ incubator at 37° C. for 3 weeks.

Figure 11C:
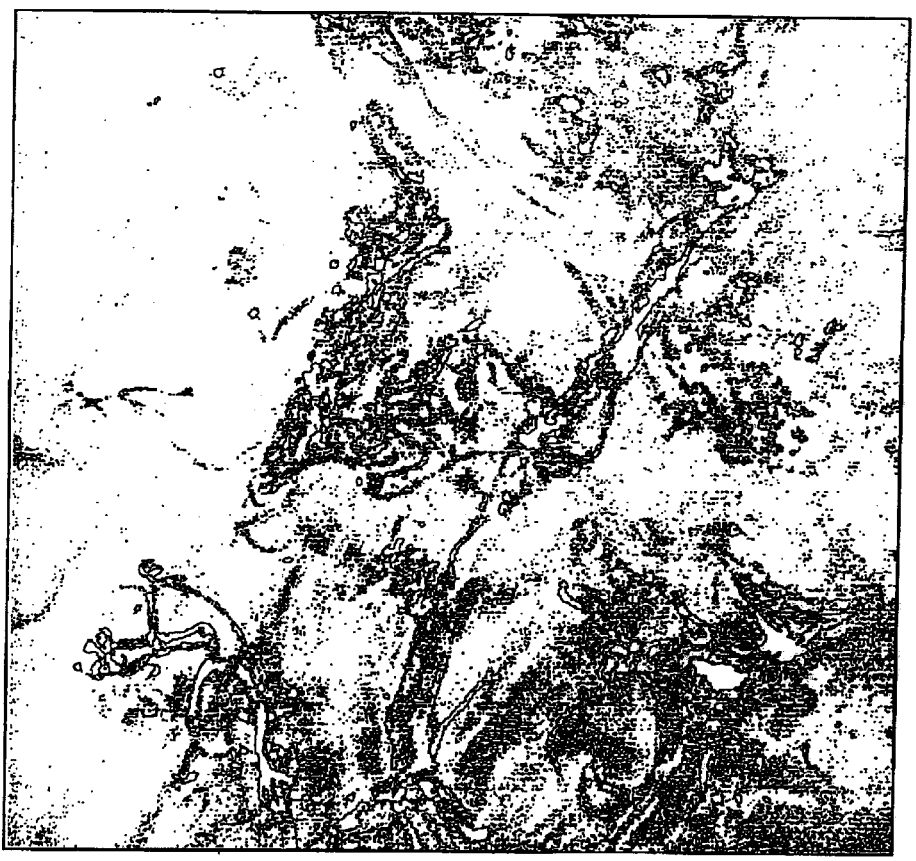
FIG. 11C is a photograph showing a support matrix formed of collagen having chondrocyte cells grown thereon, shown by immunohistochemical staining.

The support matrix holding the grown chondrocyte cells was then incubated with collagenase for 16 hours. The support matrix holding the chondrocyte cells was then centrifuged. Cells were seeded on a NUNCLON™ plate and an aliquot counted using Trypan Blue viability staining in a Bürker-Türk chamber. A microphotograph thereof is shown in FIG. 11C. The total calculated cell number was found to be $6 \times 10^6$ and the viability was >95%.

EXAMPLE 4

Animal studies were performed in the facilities of the University of Lübeck, Germany.

Four 7 mm diameter round cartilage defects were induced in the cartilage of the knees of two sheep. All interventions were performed in i.v. Ketanest/Rompun total anesthesia. The defects were induced by drilling two holes in the cartilage of the weight bearing areas of the medial femur condyle, and two holes in the area of the femuropatellar- and tibiofemural articulations. In the two areas of damage, one of each of the two holes extended through the tidemark of the cartilage and subchondral layer over the bone, while the remaining hole at each area did not extend through the tidemark of the cartilage and subchondral layer.

At the same time a piece of cartilage had been harvested from a non-weight bearing area of the sheep knees.

The chondrocyte cells produced from this cartilage were grown on a support matrix according to Example 3 for a period of six weeks.

The chondrocyte cells loaded on a Chondro-Gide® support matrix were then implanted via an arthroscopic surgery technique. Fixation occurred in one sheep by gluing the matrix to the treated area with fibrin glue, and in the other sheep the matrix was fixed using polylactide pins as described above according to the present invention.

The sheep were kept isolated and the knee was kept in a fixed dressing for one week.

Afterwards the sheep were free to move around. Evaluation of the joint showed a healing of the defect, the attachment of the cell-support matrix implant to the site of cartilage defect, and regeneration of the cartilage at the site of cartilage defect.

Figure 11D:
FIG. 11D is a photograph showing a support matrix formed of collagen, and having chondrocyte cells grown thereon in a bioreactor system, shown by immunohistochemical staining.

Although the above discussion pertains in part to a process for growing chondrocyte cells on a support matrix in glassware such as a NUNCLON™ plate and changing the growth or transplant media as required for proper cell culturing, the present invention also includes a method of growing chondrocyte cells on a support matrix in a bioreactor such as bioreactor Model No. 1302 available from MinuCells GMBH Ltd., D-93077 Bad Abbach, Germany. Using a bioreactor, constant flow of growth or transplant media is passed by the support matrix, and chondrocyte cells can be grown on the support matrix at a faster rate without having to replace the growth or transplant media, for example, every 24 to 96 hours as required when using the NUNCLON™ plate. It is understood that using such a bioreactor causes angled growth of the chondrocyte cells due to flow of the growth or transplant media through the bioreactor. A microphotograph of chondrocyte cells grown on the support matrix in the bioreactor is shown in FIG. 11D.

Culturing of the chondrocyte cells, whether cultured in glassware or on a support matrix, can take place in the growth media for the entire cell culturing process or in the transplant media for the entire cell culturing process. That is, no transfer of the chondrocyte cells from the growth media to the transplant media is required. The chondrocyte cells can be transferred from the growth media to the transplant media, and vice versa, at any point in the culturing process, depending on the particular condition of the chondrocyte cells, the stage of growth of the chondrocyte cells, and/or the condition of the patient. The chondrocyte cells, whether in the growth media or in transplant media, need to be soaked into the support matrix for a period of only about 2-3 hours before transplantation to allow attachment of a sufficient number of chondrocyte cells to the support matrix.

Where a bioreactor is not used, it is also understood that the growth media or transplant media, whichever is being used at the particular stage of the culturing process, must be replaced, for example, about every 24 to 96 hours depending, for example, on the number and viability of the cells.

While this invention has been described with respect to specific embodiments thereof, it is not limited thereto. In its most general sense, this invention encompasses essentially any article (and use thereof) comprising a support matrix, preferably flexible and preferably absorbable in a living body, which support matrix acts as a support for living cells, which are typically grown thereon for some minimum period of time and attached thereto. Such attachment may be by virtue of cell growth penetrating the surface of the matrix. Preferably, also the support matrix provides sufficient physical integrity to the implantable article to facilitate its manipulation, such as the manipulation necessary to implant it into a living body.

The subjoined claims therefore are intended to be construed to cover not only those embodiments of this invention disclosed above but also to cover all such embodiments, variants and equivalents of the invention as may be made by those skilled in the art to which the invention pertains, which embodiments, variant and equivalents are within the true spirit and scope of this invention.

What is claimed:

1. An instrument for introducing an implantable article comprising chondrocyte cells on a support matrix, to a site of cartilage defect in an animal, the instrument comprising:
   (a) a tubular outer sheath, said sheath having a proximal end adapted to be disposed at a user end of the instrument, and a distal end adapted to be disposed at the site of cartilage defect;
   (b) a handle and telescoping element disposed at least partially within said proximal end of said sheath;
   (c) an injection channel partially disposed within said handle and extending from said proximal end to said distal end of said sheath;
   (d) gripping elements attached to said telescoping element and adapted to grip and release the implantable article upon telescopic movement of said handle in said sheath; and
   (e) a needle that extends the length of the instrument and allows fluids to pass therethrough to the site of implantation.

* * * * *